US011759250B2

(12) United States Patent
Orton

(10) Patent No.: US 11,759,250 B2
(45) Date of Patent: Sep. 19, 2023

(54) ELECTRODE CONFIGURATIONS FOR ELECTRICAL FLUX DELIVERY INSTRUMENTS, AND RELATED SYSTEMS AND METHODS

(71) Applicant: INTUITIVE SURGICAL OPERATIONS, INC., Sunnyvale, CA (US)

(72) Inventor: Michael Orton, Sunnyvale, CA (US)

(73) Assignee: INTUITIVE SURGICAL OPERATIONS, INC., Sunnyvale, CA (US)

( * ) Notice: Subject to any disclaimer, the term of this patent is extended or adjusted under 35 U.S.C. 154(b) by 847 days.

(21) Appl. No.: 16/315,429

(22) PCT Filed: Jun. 23, 2017

(86) PCT No.: PCT/US2017/039056
§ 371 (c)(1),
(2) Date: Jan. 4, 2019

(87) PCT Pub. No.: WO2018/009354
PCT Pub. Date: Jan. 11, 2018

(65) Prior Publication Data
US 2019/0209233 A1 Jul. 11, 2019

Related U.S. Application Data

(60) Provisional application No. 62/359,506, filed on Jul. 7, 2016.

(51) Int. Cl.
*A61B 18/14* (2006.01)
*A61B 17/29* (2006.01)
*A61B 17/00* (2006.01)
*A61B 18/00* (2006.01)

(52) U.S. Cl.
CPC .......... *A61B 18/1445* (2013.01); *A61B 17/29* (2013.01); *A61B 18/1442* (2013.01);
(Continued)

(58) Field of Classification Search
CPC . A61B 18/1442; A61B 18/1445; A61B 17/29; A61B 2018/00071;
(Continued)

(56) References Cited

U.S. PATENT DOCUMENTS 9,055,961 B2 * 6/2015 Manzo .................. A61B 34/71
2006/0271038 A1 * 11/2006 Johnson ............. A61B 18/1442
606/45

(Continued)

FOREIGN PATENT DOCUMENTS

WO WO-2011156257 A2 12/2011
WO WO-2015094493 A1 6/2015

OTHER PUBLICATIONS

International Search Report and Written Opinion for Application No. PCT/US2017/039056, dated Sep. 22, 2017, 15 pages.
(Continued)

*Primary Examiner* — Michael F Peffley
*Assistant Examiner* — Bo Ouyang
(74) *Attorney, Agent, or Firm* — JONES ROBB, PLLC

(57) ABSTRACT

An electrosurgical instrument may comprise a pair of jaw members configured to move between an open position and a closed position. In the closed position, the pair of jaw members may be configured to exert a gripping force on material placed between working surfaces of the pair of jaw members. A first jaw member of the pair of jaw members may comprise a first electrode, and a second jaw member of the pair of jaw members may comprise a second electrode and a third electrode.

30 Claims, 9 Drawing Sheets

(52) U.S. Cl.
CPC .............. *A61B 2017/00026* (2013.01); *A61B 2017/0088* (2013.01); *A61B 2018/0063* (2013.01); *A61B 2018/00071* (2013.01); *A61B 2018/00089* (2013.01); *A61B 2018/00601* (2013.01); *A61B 2018/00875* (2013.01); *A61B 2018/1467* (2013.01)

(58) Field of Classification Search
CPC ........... A61B 2018/00089; A61B 2017/00601; A61B 2018/0063; A61B 2018/00875; A61B 2018/1467; A61B 2017/00026; A61B 2017/0088
See application file for complete search history.

(56) References Cited

U.S. PATENT DOCUMENTS

| | | | |
|---|---|---|---|
| 2009/0082769 A1* | 3/2009 | Unger | A61B 18/1445 606/52 |
| 2009/0138006 A1 | 5/2009 | Bales et al. | |
| 2012/0078247 A1* | 3/2012 | Worrell | A61B 18/1447 606/45 |
| 2013/0325031 A1 | 12/2013 | Schena et al. | |
| 2013/0325033 A1 | 12/2013 | Schena et al. | |

OTHER PUBLICATIONS

Olympus, Thunderbeat Open Extended Jaw, Versatility, Speed, and Precision—Advanced Energy Solutions for Open Surgery, 2015, 12 pages.

Vertut, Jean and Phillipe Coiffet, Robot Technology: Teleoperation and Robotics Evolution and Development, English translation, Prentice-Hall, Inc., Inglewood Cliffs, NJ, USA 1986, vol. 3A, 332 pages.

* cited by examiner

ELECTRODE CONFIGURATIONS FOR ELECTRICAL FLUX DELIVERY INSTRUMENTS, AND RELATED SYSTEMS AND METHODS

CROSS-REFERENCE TO RELATED APPLICATIONS

This application is a U.S. national stage application under 35 U.S.C. § 371(c) of International Application No. PCT/US2017/039056, filed on Jun. 23, 2017, which claims priority to U.S. Provisional Patent Application 62/359,506, filed on Jul. 7, 2016, the entire content each of which is incorporated by reference herein in its entirety.

TECHNICAL FIELD

Aspects of the present disclosure relate to electrical flux delivery instruments and related systems and methods, such as, for example, electrosurgical instruments, systems, and methods for delivering electrical and thermal energy to perform electrosurgical procedures.

INTRODUCTION

Remotely controlled surgical instruments, including both manual, laparoscopic instruments and computer-assisted, teleoperated surgical instruments (sometimes referred to as robotic surgical instruments), are often used in minimally invasive medical procedures. For example, in teleoperated surgical systems, surgeons manipulate input devices at a surgeon console, and those "master" inputs are passed to a patient side cart that interfaces with one or more remotely controlled surgical instruments coupled to the patient side cart. Based on the surgeon inputs at the surgeon console, the one or more remotely controlled surgical instruments are actuated at the patient side cart to operate on the patient, thereby creating a master-slave control relationship between the surgeon console and the surgical instrument(s) at the patient side cart.

Some surgical instruments, such as electrosurgical instruments and other types of surgical instruments, are configured to deliver a flux (e.g., electrical energy, thermal energy, ultrasonic energy, irrigation, suction, etc.) to material such as tissue, or a tissue-like material for testing purposes. Such surgical instruments are coupled to a flux supply unit, such as electrosurgical energy generating units (ESU's) in the case of an electrosurgical instrument. For instance, an ESU may generate and supply electrical flux energy to an electrosurgical instrument so that an electrosurgical energy can be applied to tissue at or near an end effector of the electrosurgical instrument. Exemplary end effectors include gripping end effectors that can perform cutting and sealing operations on, for instance, vessels and other types of tissue. Cutting and sealing operations generally rely on electrical energy from an ESU that is converted to thermal energy when the gripping end effectors grip a section of tissue.

However, sealing operations often dry out the tissue, rendering it more difficult to cut, particularly if the cutting operation is performed using electrical energy as opposed to mechanical cutting using a blade or the like. Dry tissue requires higher amounts of energy to cut than wet tissue. In addition, cutting cleanly and accurately via electrosurgical energy is more difficult with dry tissue. In addition, because of the multiple functionalities that are desired in some cases in addition to the delivery of energy from an end effector, size constraints pose challenges in the design of electrosurgical instruments for minimally invasive applications.

Thus, it is desirable to minimize the size of such instruments without negatively impacting the ability of the instrument to perform multiple functions that may require space to accommodate various actuation and other components along the instrument. It is also desirable to provide electrosurgical instrument configurations that account for changes in the material to which energy is being applied (e.g., tissue) during the course of a procedure or procedures acting on such material.

There exists a continued need to improve upon electrical flux delivery instruments, such as electrosurgical instruments, and related systems and methods for delivering electrosurgical energy to perform various surgical procedures.

SUMMARY

Exemplary embodiments of the present disclosure may solve one or more of the above-mentioned technical challenges and/or may demonstrate one or more of the above-mentioned desirable features. Other features and/or advantages may become apparent from the description that follows.

In accordance with at least one exemplary embodiment, the present disclosure contemplates an electrosurgical instrument having a pair of jaw members configured to move between an open position and a closed position. In the closed position, the pair of jaw members is configured to exert a gripping force on material placed between working surfaces of the pair of jaw members. A first jaw member of the pair of jaw members comprises a first electrode, and a second jaw member of the pair of jaw members comprises a second electrode and a third electrode.

In accordance with another exemplary embodiment, the present disclosure contemplates a surgical system comprising an electrosurgical instrument, and an electrosurgical energy supply source electrically coupled to supply electrical energy to the electrosurgical instrument. The electrosurgical instrument comprises a first jaw member comprising a first electrode, and a second jaw member comprising a second electrode and a third electrode. The first and second jaw members are configured to grasp a material between opposing working surfaces of each of the first and second jaw members, and the electrosurgical energy supply source is configured to selectively alter a polarity of each of the first, second, and third electrodes, the polarity being chosen from positive, negative, and neutral.

In accordance with another exemplary embodiment, the present disclosure contemplates a method for performing electrosurgical operations. The method includes gripping a material between the first and second opposing working surfaces of a pair of jaw members, a first jaw member of the pair of jaw members comprising a first electrode and a second jaw member of the pair of jaw members comprising a second electrode and a third electrode, and delivering electrical energy to at least two electrodes, the at least two electrodes selected from the group consisting of of the first, second, and third electrodes, wherein delivering the electrical energy induces a thermal effect in the gripped material.

In accordance with another exemplary embodiment, the present disclosure contemplates an electrosurgical instrument comprising a pair of opposing jaw members, each of the pair of jaws comprising at least one electrode configured to apply electrical energy to a material gripped between the pair of jaws. At least one of the electrodes pair of jaws comprises a surface feature configured to concentrate electrical energy.

In accordance with another exemplary embodiment, the present disclosure contemplates an electrosurgical instrument including a pair of opposing jaw members, each of the pair of jaw members comprising at least one electrode for applying electrical energy to a material gripped between opposing working surfaces of the pair of jaw members. At least one of the pair of jaw members has a geometry configured to absorb thermal energy at a portion of the respective working surface of the at least one jaw of the pair of jaw members more than other portions of the respective working surface so as to absorb thermal energy generated by material gripped between the opposing working surfaces of the jaw members.

Additional objects, features, and/or advantages will be set forth in part in the description which follows, and in part will be obvious from the description, or may be learned by practice of the present disclosure and/or claims. At least some of these objects and advantages may be realized and attained by the elements and combinations particularly pointed out in the appended claims.

It is to be understood that both the foregoing general description and the following detailed description are exemplary and explanatory only and are not restrictive of the claims; rather the claims should be entitled to their full breadth of scope, including equivalents.

BRIEF DESCRIPTION OF THE DRAWINGS

The present disclosure can be understood from the following detailed description, either alone or together with the accompanying drawings. The drawings are included to provide a further understanding of the present disclosure, and are incorporated in and constitute a part of this specification. The drawings illustrate one or more exemplary embodiments of the present teachings and together with the description serve to explain certain principles and operation.

DETAILED DESCRIPTION

Figure 1:
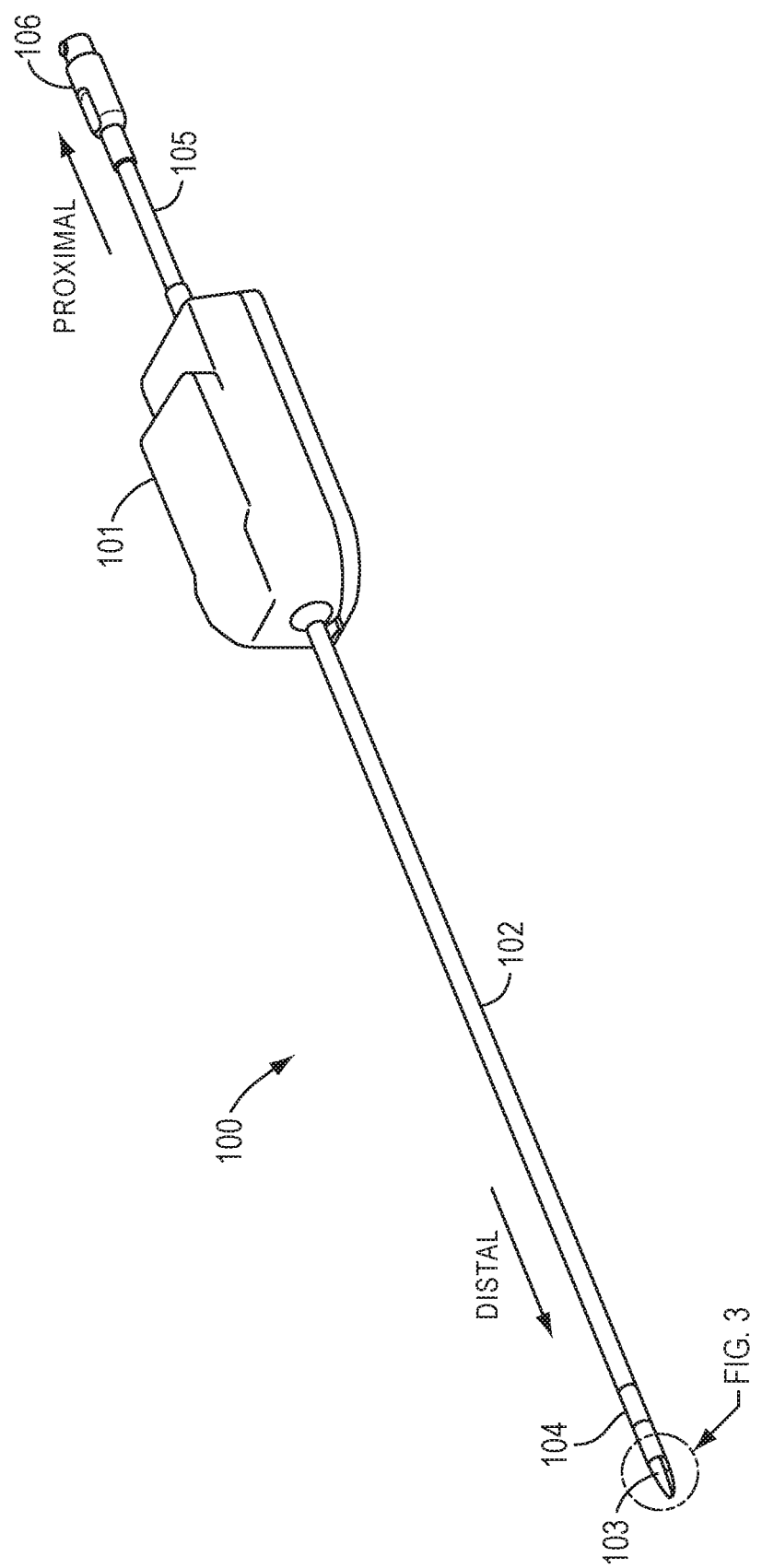
FIG. 1 is a perspective view of an exemplary embodiment of a minimally invasive electrosurgical instrument.

This description and the accompanying drawings that illustrate exemplary embodiments should not be taken as limiting. Various mechanical, compositional, structural, electrical, and operational changes may be made without departing from the scope of this description and the claims, including equivalents. In some instances, well-known structures and techniques have not been shown or described in detail so as not to obscure the disclosure. Like numbers in two or more figures represent the same or similar elements. Furthermore, elements and their associated features that are described in detail with reference to one embodiment may, whenever practical, be included in other embodiments in which they are not specifically shown or described. For example, if an element is described in detail with reference to one embodiment and is not described with reference to a second embodiment, the element may nevertheless be claimed as included in the second embodiment.

For the purposes of this specification and appended claims, unless otherwise indicated, all numbers expressing quantities, percentages, or proportions, and other numerical values used in the specification and claims, are to be understood as being modified in all instances by the term "about," to the extent they are not already so modified. Accordingly, unless indicated to the contrary, the numerical parameters set forth in the following specification and attached claims are approximations that may vary depending upon the desired properties sought to be obtained. At the very least, and not as an attempt to limit the application of the doctrine of equivalents to the scope of the claims, each numerical parameter should at least be construed in light of the number of reported significant digits and by applying ordinary rounding techniques.

It is noted that, as used in this specification and the appended claims, the singular forms "a," "an," and "the," and any singular use of any word, include plural referents unless expressly and unequivocally limited to one referent. As used herein, the term "include" and its grammatical variants are intended to be non-limiting, such that recitation of items in a list is not to the exclusion of other like items that can be substituted or added to the listed items.

In accordance with various exemplary embodiments, the present disclosure contemplates surgical instruments comprising gripping end effectors that are configured to deliver electrical energy to perform electrosurgical procedures such as sealing (cauterizing) and cutting (incision) of tissue, including but not limited to blood vessels for example. For training and/or testing purposes, the exemplary surgical instruments described herein can also be used on materials having properties similar to tissue.

In various exemplary embodiments, electrode configurations, thermal profiles, and/or geometries of gripping end effectors (e.g., a pair of jaws) can be configured to perform different procedures and to achieve variable thermal profiles during delivery of energy to a material such as, for instance, a tissue. Various changes to electrode placement, polarity, and/or geometry enable directing the flow of electrical energy in specific directions and concentrations to achieve desired effects on materials gripped between the gripping end-effectors. Various permutations of thermal properties and/or geometries of working surfaces of electrodes, for example supported by or forming jaws of an end effector, are presented for enabling more efficient electrosurgical procedures, such as sealing and cutting. For example, one or more working surfaces of the jaws of the end effector can comprise surface features that are configured to concentrate electrical energy, as further described herein. For the purposes of this disclosure, "working surfaces" are any surfaces of gripping end-effectors via which flux is delivered. In the exemplary embodiments described herein, working surfaces of gripping end effectors are working surfaces that grip material, such as tissue. For example, a lower surface of an upper jaw electrode and upper surfaces of lower jaw electrodes collectively comprise working surfaces.

In exemplary embodiments described herein, a gripping end effector of a surgical instrument comprises an upper jaw comprising one electrode, and a lower jaw comprising a pair of electrodes separated by a dielectric material. For example, the lower jaw in various exemplary embodiments has the dielectric insulating material extending centrally and longitudinally in a proximal-distal direction of the jaws with the pair of electrodes being positioned on either side of the dielectric material. Each electrode may be set to a positive, negative, or neutral potential, thereby enabling electrical energy to flow between different combinations of electrodes, depending on the intended procedure to be performed. For example, the polarities on the electrodes may be changed for different electrosurgical procedures, such as, for example, during a sealing procedure versus a cutting procedure. In various exemplary embodiments described herein, sections of the jaws can be configured to deliver the energy sufficient to perform either a sealing or a cutting procedure. For example, laterally outer portions of the working surfaces of each jaw may be configured (via electrode placement, geometry, thermal and electrical conductivity, etc.) to perform sealing procedures, and middle portions of the jaws may be configured to perform cutting procedures. In the context of the exemplary embodiments described herein, an "outer" portion is closer to the edges of a width of the jaws when viewed from a vertical cross-section, and a "middle" portion is closer to a center of the jaws.

In exemplary embodiments described herein, electrical energy can be transferred from one electrode on one side of the lower jaw, through tissue, to another electrode on the other side of the same jaw, using the tissue and an electrode on the upper (i.e. opposing) jaw as a conduit through which the energy is transferred. Such a configuration spreads the passage of current and, therefore the generation of heat, relatively evenly across the jaw during the low voltage portion of the sealing procedure. In addition, such a configuration eliminates the need for multiple wires connected to different electrodes, as electrical energy may be returned back to the ESU via the wire connected to the lower jaw. Moreover, one or both jaw electrodes can be made with varying geometries, such as, for example, sharp edges or corners configured and positioned for directing a strong electric field in a concentrated region, so as to effectively ionize and/or electrically cut targeted regions of tissue between the electrodes.

In addition, the thermal conductivity of electrodes on each jaw can be varied to create different thermal profiles in the material grasped between the jaws during sealing and cutting procedures. For example, various exemplary embodiments utilize electrodes comprising a relatively thick layer on portions of working surfaces of the jaws. The thick layer functions as a heatsink that draws heat away from those portions of the jaws. In exemplary embodiments the thick layer is provided on those portions of the jaws that are intended to perform cutting procedures such that, during a sealing operation using the jaws, excessive moisture is not lost from the material (e.g., tissue) grasped by the thick layer portions. This can permit the tissue in that region to retain moisture, and therefore to be subsequently cut more effectively as further described herein. The geometry of the jaw electrodes may further be configured such that tissue is gripped with varying pressures over the width of the working surfaces, such as, for example, with higher pressure in the middle portion of the working surfaces, which is intended for performing cutting operations.

For ease of description, various exemplary embodiments set forth below describe electrosurgical instruments that are remotely controlled (e.g., via teleoperation or manually) by a surgeon, and powered by energy supply sources or generators that deliver of an electrical flux (e.g., such as electrosurgical energy for cautery procedures, which may comprise, for example, a voltage range from 50 volts to 1000s of volts, for example, 100s of volts to 1000s of volts, and the current ranges from 0.2 amps (A) to 8 A, for example from 0.5 A to 4 A. In exemplary embodiments, power ranges from 10 Watts to a few hundred Watts, for example from 10 Watts to 300 Watts, or from 10 Watts, to 250 Watts, or from 10 Watts to 200 Watts.

With reference now to FIG. 1, a perspective view of a minimally invasive surgical instrument 100 is illustrated. The directions "proximal" and "distal" are used herein to define the directions as shown in FIG. 1, with distal generally being in a direction further along a kinematic arm or closest to the surgical work site in the intended operational use of the instrument 100, for example, in use for performing surgical procedures. As shown in FIG. 1, the instrument 100 generally includes a force/torque drive transmission mechanism 101, an instrument shaft 102 mounted to the transmission mechanism 101, an end effector 103 disposed at the distal end of the instrument 100, and an optional articulation wrist 104 disposed at a distal end of the shaft 102 to support the end effector 103 on the shaft 102. End effector 103 can be one of a variety of types. For example, end effector 103 can be configured to deliver electrical flux energy to be used for electrosurgical procedures on tissue during minimally invasive surgical procedures. End effector 103 may operate in a monopolar or bipolar mode to deliver electrical flux, as well as in harmonic, laser, and ultrasonic modes to deliver types of energy other than electrical energy. For example, monopolar and bipolar end effectors are capable of treating tissue with heat produced by electrical energy while cutting, shearing, grasping, engaging, or contacting tissue. An exemplary embodiment of a gripping end effector is further described with reference to FIG. 3.

Figure 2:
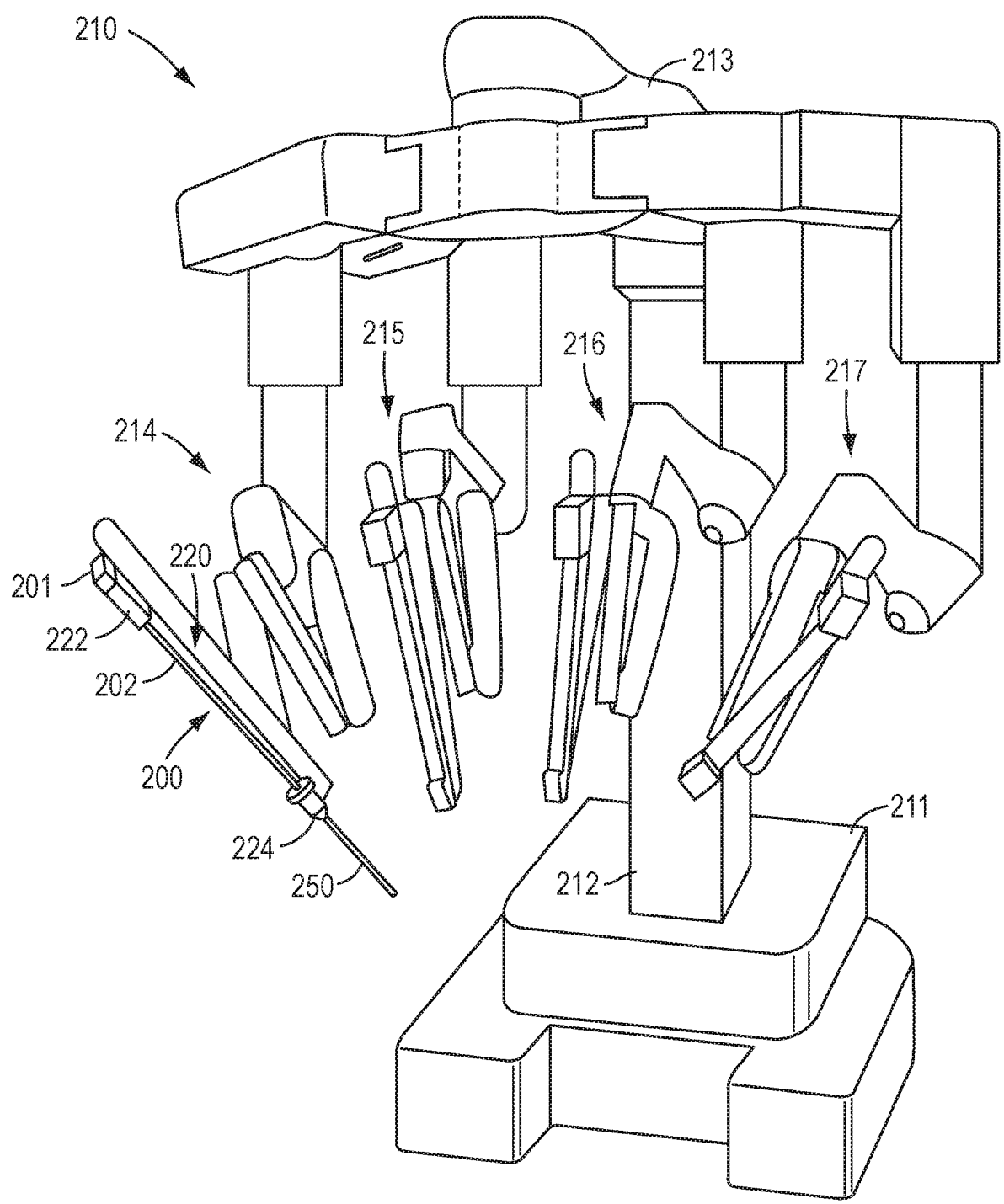
FIG. 2 is a perspective view of an exemplary embodiment of a patient side cart.

As discussed above, in accordance with various exemplary embodiments, surgical instruments of the present disclosure are configured for use in teleoperated, computer-assisted surgical systems (sometimes referred to as robotic surgical systems). Referring now to FIG. 2, an exemplary embodiment of a patient side cart 210 of a teleoperated, computer-assisted surgical system, to which surgical instruments are configured to be mounted for use, is shown. Such a surgical system may further include a surgeon console (not shown) for receiving input from a user to control instruments of patient side cart 210, as well as an auxiliary control/vision cart (not shown), as described in, for example, U.S. Pub. No. US 2013/0325033, entitled "Multi-Port Surgical Robotic System Architecture" and published on Dec. 5, 2013, and U.S. Pub. No. US 2013/0325031, entitled "Redundant Axis and Degree of Freedom for Hardware-Constrained Remote Center Robotic Manipulator" and published on Dec. 5, 2013, each of which is hereby incorporated by reference in its entirety. Non-limiting, exemplary embodiments of teleoperated surgical systems with which the principles of the present disclosure may be utilized include the da Vinci® Si (model no. IS3000) da Vinci® Si Surgical System, Single Site da Vinci® Surgical System, or a da Vinci® Xi Surgical System, available from Intuitive Surgical, Inc. of Sunnyvale, Calif. However, persons having ordinary skill in the art will appreciate that the present disclosure can be applied to a variety of surgical systems including automated or manual (hand-held) laparoscopic surgical systems.

Patient side cart 210 includes a base 211, a main column 212, and a main boom 213 connected to main column 212. Patient side cart 210 also includes a plurality of jointed set-up arms 214, 215, 216, 217, which are each connected to main boom 213. Arms 214, 215, 216, 217 each include an instrument mount portion 220 to which an instrument may be mounted, such as instrument 200, which is illustrated as being attached to arm 214. Arms 214, 215, 216, 217 further include manipulator portions that can be manipulated during a surgical procedure according to commands provided by a user at the surgeon console. In an exemplary embodiment, signal(s) or input(s) transmitted from a surgeon console are transmitted to a control/vision cart, which interprets the input(s) and generate command(s) or output(s) to be transmitted to the patient side cart 210 to cause manipulation of an instrument 200 and/or portions of arm 214 to which the instrument 200 is coupled. Those having ordinary skill in the art would understand that the processor/controller functionality need not be included in an auxiliary/vision cart separate from the patient side cart and surgeon console, but rather could be on a different piece of equipment, on the surgeon console or patient side cart, or distributed between those components.

Instrument mount portion 220 comprises an actuation interface assembly 222 and a cannula mount 224, with a force transmission mechanism 201 of instrument 200 connecting with the actuation interface assembly 222. Cannula mount 224 is configured to hold a cannula 250 through which shaft 202 of instrument 200 may extend to a surgery site during a surgical procedure. Actuation interface assembly 222 contains a variety of drive and other mechanisms that are controlled to respond to input commands at the surgeon console and transmit forces to the force transmission mechanism 201 to actuate instrument 200, as those skilled in the art are familiar with.

Although the exemplary embodiment of FIG. 2 shows an instrument 200 attached to only arm 214 for ease of viewing, an instrument may be attached to any and each of arms 214, 215, 216, 217. An instrument 200 may be a surgical instrument with an end effector, such as instrument 100 as discussed above with reference to FIG. 1. A surgical instrument with an end effector may be attached to and used with any of arms 214, 215, 216, 217. However, the embodiments described herein are not limited to the exemplary embodiment of FIG. 2, and various other teleoperated, computer-assisted surgical system configurations may be used with the exemplary embodiments described herein.

Referring again to FIG. 1, the transmission mechanism 101 transmits received actuation inputs, for example, from a patient side cart in computer-assisted surgical systems or manually, to resulting torques and forces to effect movement of the instrument shaft 102, wrist 104, end effector 103, and/or associated components, to accomplish various motions, potentially resulting in a multiple-degrees-of-freedom (multi-DOF) actuation of the surgical instrument. For example, the transmission mechanism 101 can be controlled via inputs (e.g., torque inputs) to roll shaft 102, and consequently end effector 103 (roll DOF), open and close jaws of the end effector 103 (grip or clamp DOF), and articulate wrist 104 (articulation DOF), among others. In various exemplary embodiments, the wrist 104 can be configured for two-DOF articulation in orthogonal directions to provide both "pitch" and "yaw" movement of end effector 3 (yaw being arbitrarily defined as being the plane of motion of the end effector jaws, pitch being orthogonal to yaw).

The transmission mechanism 101 also can accommodate electrical conductors (not shown in FIG. 1) to receive electrosurgical energy via connector 106 that is electrically coupled to an electrical flux generation source such as, for example, an electrosurgical supply unit (ESU). The ESU may be remotely controlled by a surgeon via a surgeon console, as discussed above. Electrical conductors include wires and other types of conductors (for example, ultrasonic) for actuating and for delivering flux (for example, electrical, thermal, or ultrasonic energy) from one or more ESU's to end effector 103, whereupon the flux may be used to perform electrosurgical procedures, such as fuse, cauterize, or cut tissue and/or tissue-like materials. The conductors can be routed from the transmission mechanism 101, down the instrument shaft 102 to the end effector 103.

Additional details regarding exemplary, but non-limiting, embodiments of electrosurgical instruments that include a transmission mechanism and a jawed end effector with opposing electrode assemblies configured for performing fusing and cauterizing (e.g., vessel sealing) are disclosed in U.S. Pat. No. 9,055,961 B2, and being titled "FUSING AND CUTTING SURGICAL INSTRUMENT AND RELATED METHODS," and issued Jun. 16, 2015, which is hereby incorporated by reference herein in its entirety.

Figure 3:
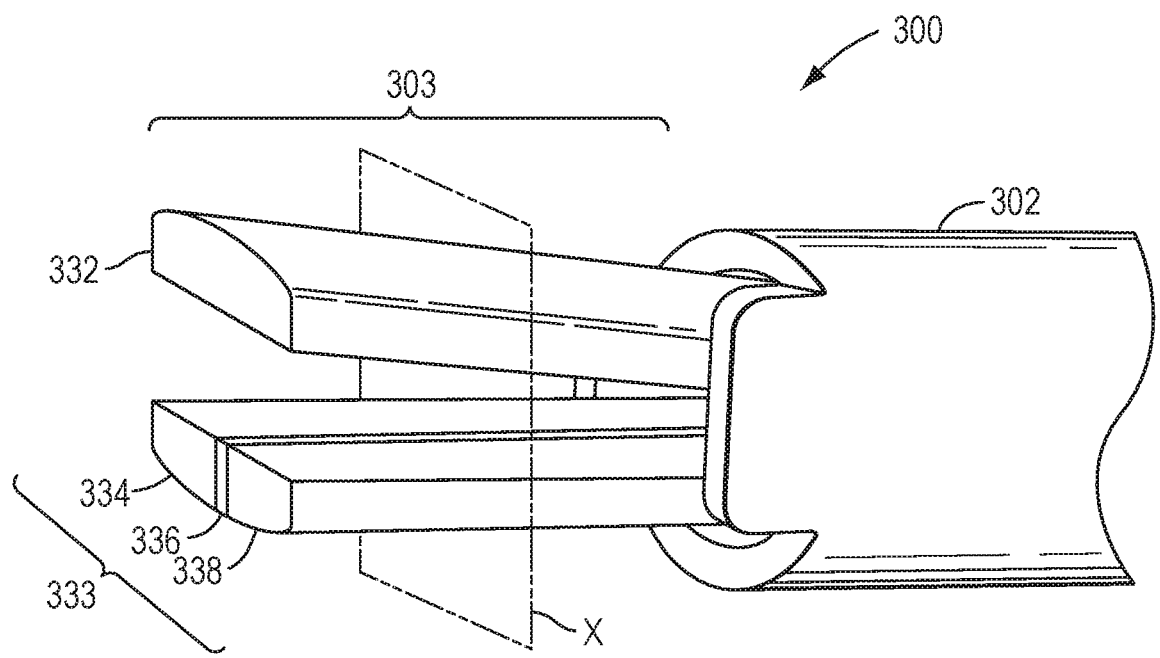
FIG. 3 is a magnified view of a distal end portion of an exemplary embodiment of a surgical instrument with a gripping end effector in an open position.

FIG. 3 depicts a magnified perspective view of a distal end portion of an exemplary embodiment of a surgical instrument 300 with a gripping end effector 303 in an open position. In this embodiment, gripping end effector 303 comprises a pair of opposing jaws including an upper jaw 332 and lower jaw 333, with the upper and lower relative positions being with respect to the orientation shown in the figures. Each of the jaws may be referred to as a jaw or jaw member herein. As shown, lower jaw 333 comprises lower jaw portions 334, 336, and 338, which form an integral structure. Upper jaw 332 and lower jaw 333 may be opened, i.e. moved away from each other, and closed, i.e. moved toward each other, via mechanical actuation elements routed through surgical instrument 300, such as from the transmission housing along the instrument shaft 302 and to end effector 303. Further, each jaw 332, 333 can be configured as one or more electric terminals, or "electrodes" via wires routed through shaft 302, such that electrical energy is delivered to each electrode to perform electrosurgical procedures as further described herein. For instance, upper jaw 332 may be configured as a first electrode, lower jaw portion 334 configured as a second electrode, and lower jaw portion 338 as a third electrode. Consequently, lower jaw portion 336 comprises a dielectric material that provides an insulating layer between two lower jaw portions 334 and 338 configured as electrodes. Electrical energy delivered to each of the 3 electrodes, as well as the polarity of the energy, i.e. a positive or negative voltage, can be switched in various configurations to enable upper and lower jaws 332, 333 to achieve different effects.

For example, surgical instrument 300 may comprise a tissue sealing and cutting end effector. To perform a sealing procedure, gripping end effector 303 is used to grasp tissue (such as, e.g., a vascular bundle or skeletonized vessel that may, for example, be up to 7 mm thick) or other material between upper and lower jaws 332, 333, and apply electrical energy via input controls, for example, at a surgeon's console of a teleoperated surgical system or otherwise from a generator source (ESU). The tissue may be grasped between working surfaces of jaws 332, 333. The application of electrical energy at a specific voltage (and, in the case of A/C voltage, frequency) generates heat in the material due to the resistance inherent to the material. In the case of tissue, the heat causes the proteins within the grasped tissue to melt until they are cross-linked, thereby forming a permanent weld or seal. The polarities of the electrodes (i.e. positive, negative, or neutral) and the amount (i.e. amplitude) of energy delivered thereto can be further adjusted to perform a cutting procedure. For instance, polarities and amplitudes of voltage can be adjusted using a control panel at the ESU, or by a surgeon operating a console, or any other method, as further described herein.

Figure 4:
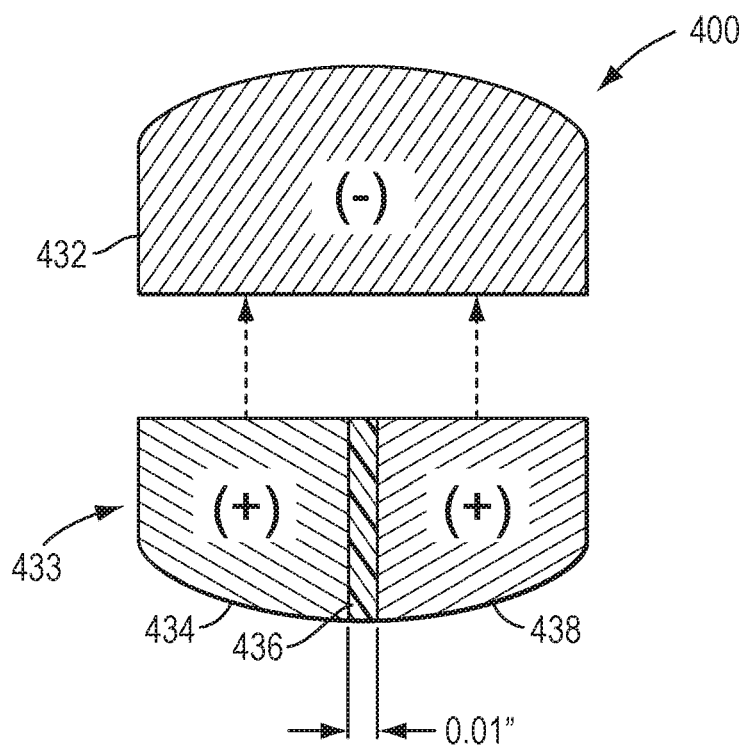
FIG. 4 is a cross-section view of an exemplary embodiment of a gripping end effector comprising electrodes configured to deliver electrosurgical energy for performing a sealing procedure.
Figure 5:
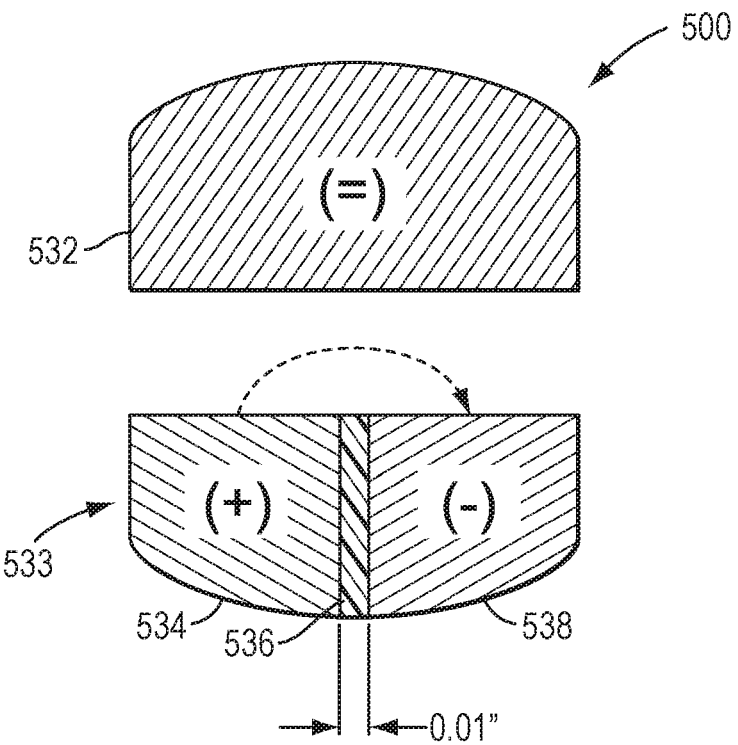
FIG. 5 is a cross-section view of an exemplary embodiment of a gripping end effector comprising electrodes configured to deliver electrosurgical energy for performing a cutting procedure.

FIGS. 4 and 5 depict transverse cross-section views (taken in plane X shown in FIG. 3) of exemplary gripping end effectors 400 and 500 having jaws with electrode portions configured for performing vessel sealing and cutting procedures, respectively. With reference to FIG. 4 depicting the configuration used for the sealing procedure, upper jaw 432 is energized as a negative electrode (via, for instance, a control panel of an ESU or surgeon's console), and lower jaw portions 434 and 438 are energized as positive electrodes. Dielectric portion 436 maintains an insulating layer between lower jaw portions 434 and 438. Thus, when flux in the form of a voltage or potential is applied to jaws 432, 434, and 438 configured as electrodes as shown, a flow of energy (i.e. positive current) shown generally by the dashed arrows is directed from both lower jaw portions 434, 438 to top jaw 432.

Figure 6:
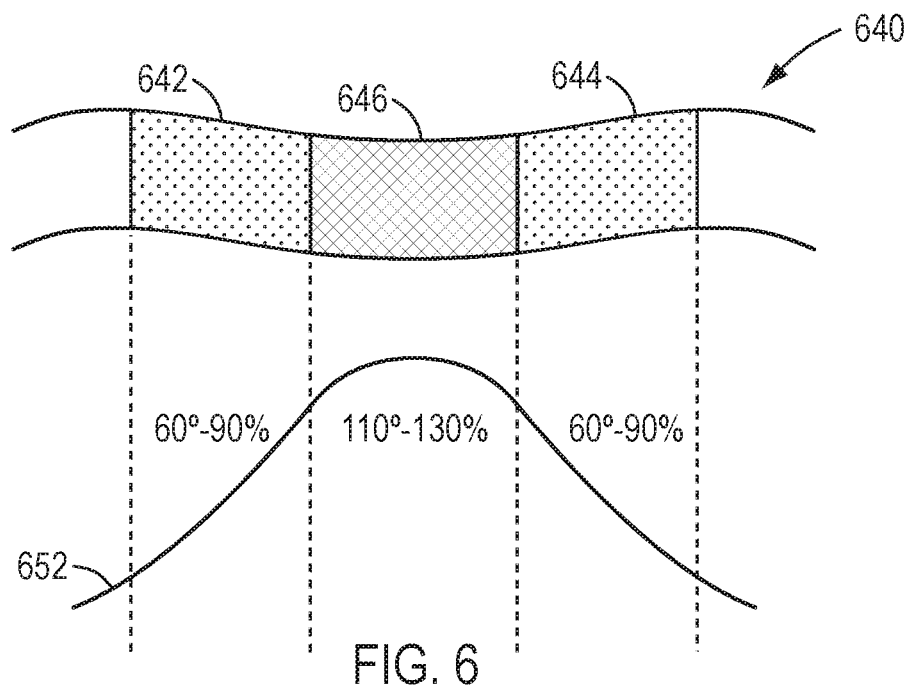
FIG. 6 depicts an exemplary temperature profile for sealing and cutting tissue.

In exemplary embodiments, the flow of energy caused by the electrode configuration of FIG. 4 results in heating a resistive material grasped by the gripping end-effector, such as tissue. Referring now to FIG. 6, an exemplary temperature profile is shown for sealing and cutting a tissue, such as a blood vessel 640. In an exemplary seal and cut procedures, vessel 640 is intended to be sealed at two seal regions 642 and 644, and cut at cut region 646. A temperature curve 652 depicts exemplary target temperature ranges induced in grasped material for each of these procedures. For example, a melting effect of tissue proteins is achieved in a range from 60° C. to 90° C. Specifically, electrical energy delivered via electrodes of a gripping end effector is conducted through vessel 640, and the natural-occurring resistance of vessel 640 causes seal regions 642, 644 to heat to a level that enables crosslinking of the proteins therein, to form a seal. The sealing procedure allows tissue to remain grossly intact, while destroying cells at the point of contact, and sealing smaller vessels, thereby stopping capillary and small-arterial bleeding.

Further, electrosurgical cutting generally requires a higher temperature, as a larger amount of electrical energy must be channeled through a small portion of the tissue in order to achieve cell lysis or vaporization. Thus, cutting is achieved in a temperature range from 110° C. to 130° C. These temperature profiles are merely exemplary, and can vary depending upon the type of tissue selected between, for example, high-impedance tissue, such as fat and scar tissue, versus low-impedance tissue, such as vascular tissue. It should be understood that the temperature profiles in the grasped material are induced by application of a level of electrosurgical energy (i.e. voltage) to the electrodes in jaws 432, 433, and such energy level may be adjusted by an ESU to match a desired temperature range depending, for example, on the tissue type and procedure being performed. It should further be understood that, generally, the seal temperature of 60° C. to 90° C. occurs during a seal procedure, and the cutting temperature of 110° C. to 130° C. occurs during a cut procedure. For example, different voltage amplitudes and generator modes are delivered from a flux generator such as an ESU to the electrodes of gripping end effector jaws during each operation, as further described below and with reference to FIGS. 10A-10B.

With reference now to FIG. 5, an exemplary electrode energization is shown for a cutting procedure. Upper jaw 532 is configured as a neutral electrode (depicted by the =symbol), and lower jaw portions 534 and 538 are configured as negative and positive electrodes, respectively. In other words, lower jaw portions 534 and 538 have opposite polarities. Such a configuration creates a capacitive coupling to establish electrical current in upper jaw 532 despite not being directly in contact with the lower jaw portions 534 and 538 configured as active electrodes. Capacitive coupling generally occurs when electric current is transferred from an active electrode, through intact insulation, and into adjacent conductive materials, without direct contact. In other words, capacitive coupling in upper jaw 532 induces an energy flow (i.e. current) through upper jaw 532, such that electrical energy attempts to travel from the electrode of lower jaw portion 534 to the electrode of lower jaw portion 538, via any material gripped between jaws 532, 533, such as tissue of a vessel. As the cutting procedure generally requires a higher temperature (as depicted in, e.g., FIG. 6), the voltage or potential between opposite electrodes may be higher for the cutting procedure described with reference to FIG. 5 than for the sealing procedure described with reference to FIG. 4.

Those having ordinary skill in the art will understand, in light of this disclosure, that various combinations of voltages and waveforms (as depicted in, for instance, FIGS. 10A-10B) may be applied to the electrodes forming the jaw portions 532, 534, and 538 in order to effect various procedures utilizing end effector 500, depending on what application is desired. Moreover, voltages and waveforms applied to the electrodes can be adjusted based on the specific configurations and geometries of the instruments and their end effectors, as one having ordinary skill in the art would appreciate based on the present disclosure and principles of procedure disclosed herein.

The ability to switch polarities of the electrodes of the upper jaw and bottom jaw portions may use at least three independent electrical paths to be routed from an ESU through the shaft of the surgical instrument. In some embodiments, a single wire can be routed to each electrode, and a wrist portion (such as wrist portion 104 depicted in FIG. 1) may be maintained as a return electrode. In other exemplary embodiments, a single wire can be routed to each of the two electrodes on the lower jaw member, with the electrode on the upper jaw member being maintained at a neutral potential, or configured as a return electrode, i.e. to return electrical energy to the ESU via the wrist portion, for example. Maintaining one electrode as a neutral electrode further reduces the number of wires required during construction or assembly of the electrosurgical instrument. Moreover, the wrist can remain isolated to prevent unintended tissue effects in locations not on the jaw. Further, in various exemplary embodiments, each lower jaw electrode may be manufactured from steel, thereby maintaining uniform electrical conductivity and thermal properties, while the dielectric material may be manufactured from plastic, such as ULTEM™, (PTFE) (e.g., Teflon™), or from ceramics. The plastics may be constructed by overmolding, while the ceramics may be constructed using flame spray deposition or jigsaw piece assembly. A thickness t of the dielectric material between the lower jaw electrodes may range, in some embodiments, between 0.005" to 0.0625" in thickness. Generally, the larger the gap, the higher the voltage required to induce a current flow between the lower jaw electrodes, which may make control over tissue effects more challenging. Consequently, the thickness of the dielectric may be between 0.010" to 0.020". Moreover, although the shape of the dielectric material is depicted as a generally straight and vertically oriented strip, other shapes are possible, such as an L-shape or T-shape, so as to increase structural strength of the lower jaw portion, while maintaining dielectric separation between the two lower electrodes.

In some exemplary embodiments, electrosurgical seal and cut procedures may be performed under the control of a surgeon, in which case the surgeon initially sets the electrode polarities, supplied waveforms and/or voltages to perform a sealing procedure. Then, the surgeon determines when the sealing procedure is completed, and thereafter modifies the electrode polarities to perform a cutting procedure. Alternatively or in addition to such surgeon control, sensors may be used to sense differing stages of the seal and cut procedure. For example, a sensor may be used to determine when the sealing procedure is completed, and to promulgate an automatic initiation of the cutting procedure thereafter. The sensors may measure, for example, a tissue impedance and/or a phase angle of electrical energy (i.e., current) returned via a return electrode, which can indicate the progress of the sealing procedure. For example, a rate of change of impedance or phase angle of the return energy may be correlated with known rates of change for different tissue types and thicknesses, thereby enabling a determination of when the sealing is completed. In some exemplary embodiments, a time derivative of current flowing through the tissue may be monitored to determine when to trigger a switch from the sealing procedure to the cutting procedure. Sensors for detecting these values may be positioned within the surgical instrument itself, or within an ESU or other component of an electrosurgical system. In some embodiments, a surgeon operating an electrosurgical system may be provided with real-time progress data, and manually trigger the cutting procedure upon being provided an indicator that the sealing procedure is complete. Various combinations of surgeon control and automated/sensor-based controls are envisioned and considered to be within the scope of the present disclosure.

Referring again to FIG. 6, for the cutting procedure, the lower end of the temperature range (e.g., ~110° C.) performs a more gentle cutting procedure that is generally effected by inducing cell lysis, i.e. water expands to burst cell membranes exposed to these temperatures. At the higher end of the temperature range (e.g., ~130° C.), a more aggressive cutting procedure occurs through the vaporization of tissue. At this higher energy level, arcing may occur, which can cause current to flow through the tissue and result in potential charring of tissue. Thus, exposing the tissue to large amounts of energy may be undesirable. Moreover, this requirement for greater energy is compounded by the increased resistance of the tissue caused by moisture escaping the tissue during the sealing procedure. Therefore, more input energy is desirable in the cutting procedure to maintain relatively constant output energy. To achieve a large amount of directed energy in a small region, the present disclosure contemplates altering the geometry of the gripping end effector using, for instance, sharpened corners or edges on portions of the working surfaces of the jaw members.

Figure 7:
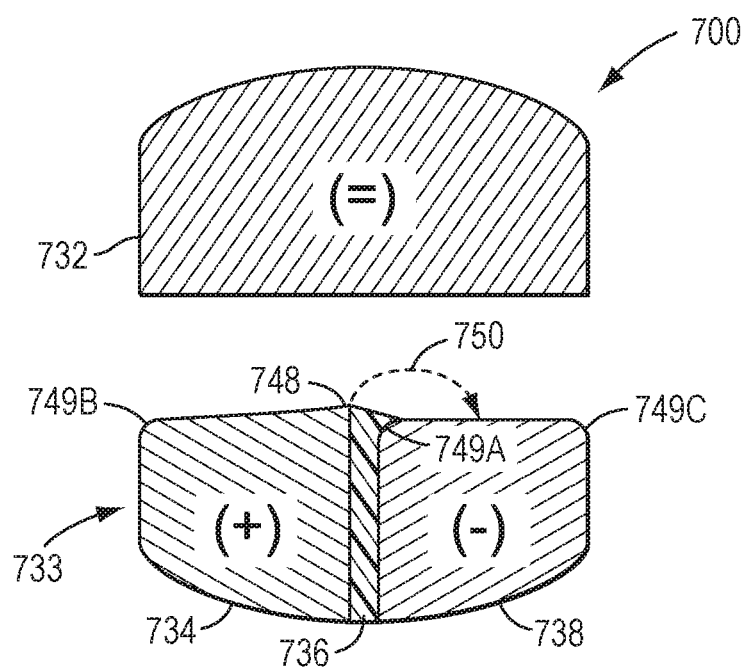
FIG. 7 is a cross-section view of an exemplary embodiment of a gripping end-effector with a sharp edge for concentrating electrical energy.
Figure 8:
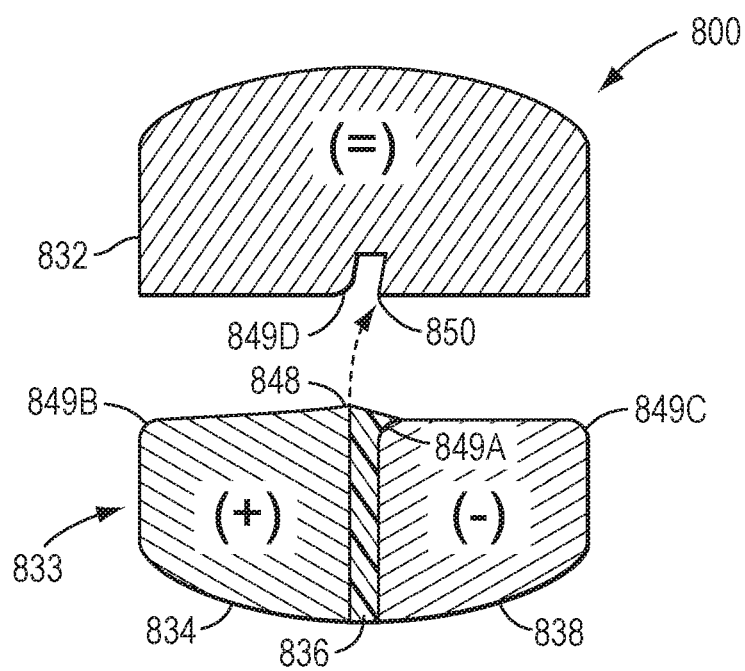
FIG. 8 is a cross-section view of another exemplary embodiment of a gripping end-effector with sharp edges for concentrating electrical energy.

FIGS. 7 and 8 depict cross-section views of exemplary embodiments of gripping end-effectors having jaw geometries that are configured for directing and enhancing energy flow in predetermined regions. With reference to FIG. 7, a working surface of lower jaw 733 (i.e. upper surface) comprises a sharp edge 748 (also "sharp corner 748") positioned on a corner of lower jaw portion 734 adjacent to the electrically insulating dielectric portion 736. In contrast, other edges 749A, 749B, and 749C of the working surface of lower jaw 733 are rounded. Changing the shape of the electrodes in this manner serves to induce high and low electric fields in specific parts of the working surface of lower jaw 733. For example, this positioning of the sharp edge 748 can be proximate a desired cut region of a material grasped by end effector 700, such as region 646 of vessel 640 depicted in FIG. 6. Other types of surface features, positions thereof, and desired locations for concentrating the electric field would be appreciated by those having ordinary skill in the art in light of this disclosure. In either case, as current flow (depicted generally by the dashed arrow) depends, in part, on a strength of a local electric field that is closest in distance to an opposing electrode, the sharp corner can create a concentration of the local electric field, thereby increasing the amount of output energy for a given amount of input energy. In other words, with respect to the exemplary embodiment of FIG. 7, a sharp edge 748 on lower jaw portion 733 induces a high concentration of electric field in a small area, and increases a probability of energy flowing from that specific area (as indicated by the dashed arrow), thereby increasing the temperature to cut tissue in that region. Such a physical configuration can also increase the potential to "arc" a current flow near sharp corner 748, which in turn can vaporize the tissue adjacent to sharp corner 748, which can be more effective at cutting the tissue. In contrast, the resultant lower electric field on the other parts of the lower jaw 733 reduces the energy potential adjacent to regions of the tissue that are not intended to be cut, and minimizes the probability of energy flowing into these areas. This can result in a more reliable and accurate cutting procedure that uses less overall input energy.

With reference to FIG. 8, the working surface of lower jaw 833 has a sharp edge 848 (also "sharp corner 848") positioned adjacent to the electrically insulating dielectric portion 836, while other edges (or corners) 849A, 849B, and 849C of lower jaw 833 are rounded. Changing the shape of the electrodes in this manner serves to induce high and low electric fields in specific parts of the lower jaw 833, as described above. Furthermore, the working surface of upper jaw 832 (i.e. lower surface in the orientation of the figures) is similarly constructed with a sharp corner 850, which also helps concentrate the electric field in a specific area of the lower surface of upper jaw 832. For example, as current flow depends, in part, on a strength of a local electric field that is closest in distance to an opposing electrode, the opposing sharp corners 848, 850 can induce a high concentration of electric field in a small area. Thus, current is more likely to flow in the direction of the dashed arrow, i.e. from sharp corner 848 to sharp corner 850, before being channeled back down to electrode 838, thereby increasing the temperature to cut tissue in a smaller region. In contrast, the resultant lower concentrations of electric fields on the rounded corners 849A, 849B, 849C, 849D reduce the energy potential adjacent to regions of the tissue that are not intended to be cut, and minimizes the probability of energy flowing into these areas. This can result in a more reliable and accurate cutting procedure that uses less overall input energy. It should be noted that these locations are non-limiting examples, and other locations of sharp versus rounded edges may be selected based on specific electrosurgical procedures and the energy potential requirements thereof, by those of ordinary skill in the art in light of this disclosure.

Various exemplary embodiments of the present disclosure include configuring electrodes of a gripping end effector to achieve desirable thermal properties. For example, in accordance with various exemplary embodiments, the electrode jaws can be configured such that the thermal mass varies over differing portions. By selectively configuring the portions and their respective thermal masses, the resulting thermal properties and applied thermal energy can be varied as desired.

In an exemplary application, the thermal mass toward a center of one or both jaws can be larger than the thermal mass at outer lateral portions of the jaws. As discussed above, during a sealing operation, moisture escapes the tissue due to the heat applied. Because the sealing region is immediately adjacent to the cutting region, the resultant increase in resistance of the tissue renders the tissue tougher to cut, resulting in an increase in energy in order to perform a subsequent cutting operation. To account for this, exemplary embodiments described herein modify the thermal conductivity properties of the working surfaces of the gripping end effector, so as to localize energy output in regions of the working surfaces corresponding to where sealing of the grasped material is desired. The thermal conductivity of each working surface can be further modified so as to minimize energy output in the regions of the working surfaces corresponding to where cutting of the material is desired. In this way, excess moisture can be inhibited or prevented from escaping at the region of the material, such as tissue, which is placed in the region of the jaws of the end effector where cutting is intended to occur, permitting a cleaner cut with less overall energy input to the electrosurgical instrument.

Figure 9A:
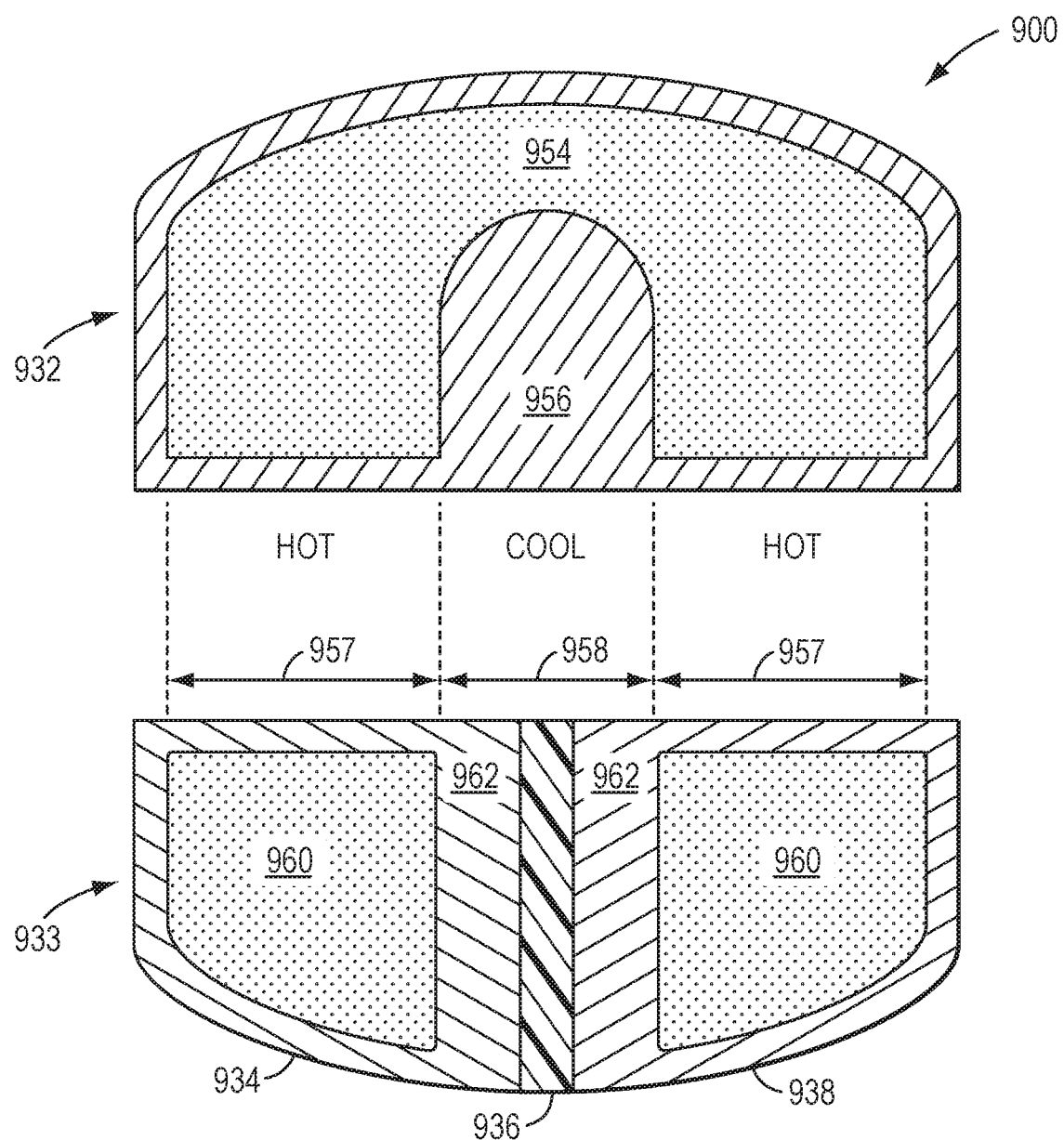
FIG. 9A is a cross-section view of an exemplary embodiment of a gripping end-effector schematically depicting thermal conductivity of the end effector jaw electrodes.
Figure 9B:
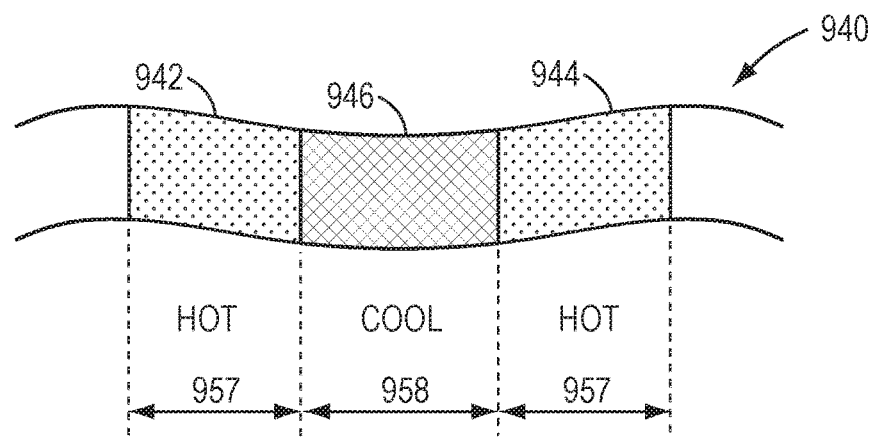
FIG. 9B is an exemplary thermal profile of a tissue grasped between gripping end effectors during application of electrical energy.

FIG. 9A depicts a transverse cross-section view of an exemplary embodiment of opposing electrode jaws of a gripping end effector 900 that exhibits variable thermal conductivity resulting from the thermal mass distribution configuration of the jaws. FIG. 9B illustrates an exemplary thermal profile of a material 940 gripped between the jaws of gripping end effector 900. For example, material 940 may comprise vessels or other body tissue, and may be referred to herein as "material 940," "vessel 940," or "tissue 940." With reference to FIG. 9A, an upper jaw 932 comprises an outer shell 956 made of an electrically and thermally conductive material surrounding an inner core 954 made of an electrically and thermally non-conducting material. Lower jaw 933 is similarly constructed, with each lower jaw portion 934, 938 comprises an outer thermally and electrically conductive shell 962 surrounding a non-conductive core 960. Further, the shell 956 of upper jaw 932 is disposed in a thin layer at regions 957 of the lower surface of upper jaw 932, and in a significantly thicker layer at region 958. Similarly, shells 962 are disposed in a thinner layer at regions 957 of an upper surface of each of lower jaw portions 934, 938 and at the outsides thereof, while being deposited in a significantly thicker layer at region 958, i.e. adjacent to the insulating dielectric portion 936. Consequently, a thick, thermally conductive middle region of both upper and lower jaws 932, 933 is formed in region 958.

In an exemplary embodiment, the material of the shells 956, 962 may be, for example, steel and other metals, or other electrically conductive materials such as, for example, carbon infused polymers. The material of the cores 954, 960 may be, for example, ULTEM™, TEFLON™, ceramic, etc. Moreover, it should be understood that the figures are not drawn to scale, and the thickness of shells 956, 962 within region 958 may be 0.010" thick at the thin layer, and as thick as the entire jaw for the thicker layer. The thickness of the electrode shell generally varies depending on how much heat needs to be drawn from the tissue.

Such a distribution of materials comprising core 954 and shell 956 on upper jaw 932 and materials 960, 962 on lower jaw 933 enable a varying thermal profile across regions 957, 958 when energy is applied to end effector 900 while end effector 900 is gripping a resistive material, such as tissue. For example, the thin conductive layers of shells 956, 962 in regions 957 heat up quickly when an electrical potential is applied to jaws 932, 933 while gripping tissue, such as during a sealing operation. Meanwhile, the thick conductive layers of shells 956, 962 in region 958 act as a heatsink, drawing thermal energy away from the working surfaces of jaws 932, 933. Consequently, during use of the jaws for sealing tissue, the tissue in grasped within regions 957 intended for sealing can be sealed at a higher surface temperature of shells 956, 962, while the lower temperature of shells 956, 962 at region 958 prevents excessive moisture from escaping from the region of the tissue intended to be cut.

For instance, referring now to FIG. 9B, an exemplary thermal profile 966 is shown for a tissue such as a vessel 940 intended to be grasped and sealed with end effector 900. Generally, an ESU delivers a specific amount of flux, e.g. voltage, to each electrode, and material grasped between the working surfaces of the electrodes heats up due to the voltage. However, the varying thickness of thermally conductive shells 956, 962 enables different portions of the material grasped between the working surfaces to be warmed at different rates or to different temperatures. For example, a portion of a material such as tissue that is intended to be sealed by the thinner regions of shells 956, 962 (i.e. regions 957) to warm up much faster than the surfaces at regions 958 due to the aforementioned heatsink. As a consequence, at the end of the sealing operation, the thermal profile 966 across the tissue 940 that is grasped by end effectors 900 exhibits a higher temperature at the portions 942, 944 that are intended to be sealed by regions 957 of the working surfaces, versus the lower temperature at the portion 946 that is intended to be cut at region 958 of the working surfaces. In other words, during the sealing operation, the temperature of portions 942, 944 of vessel 940 remains within a range from 60° C. to 90° C., while the temperature of portion 946 of vessel 940 is significantly lower. Thus, when the electrical circuit is switched (by, for instance, an ESU or surgeon operating an ESU via a console) to configure the electrodes of end effector 900 to perform a cutting operation, sufficient moisture may have been preserved in portion 946 of tissue 940, thereby facilitating a clean cut as energy is applied to perform the cutting operation. Although not wishing to be bound by any particular theory, the inventors believe the preserved moisture can help, for instance, by providing an ionization path for cells within portion 946. Moreover, during the cutting operation, a higher amount of energy is generally applied as described above. Thus, the tissue absorbs heat faster than the heatsink, enabling higher temperatures to be achieved in the cutting portion 946.

Figure 10A:
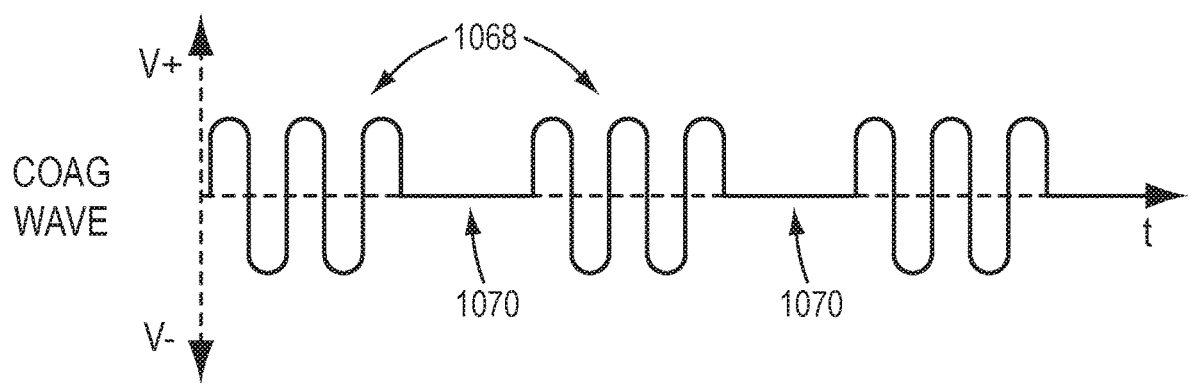
FIGS. 10A-10B depict exemplary coagulation and cut waveforms for enabling sealing and cutting procedures, respectively.
Figure 10B:
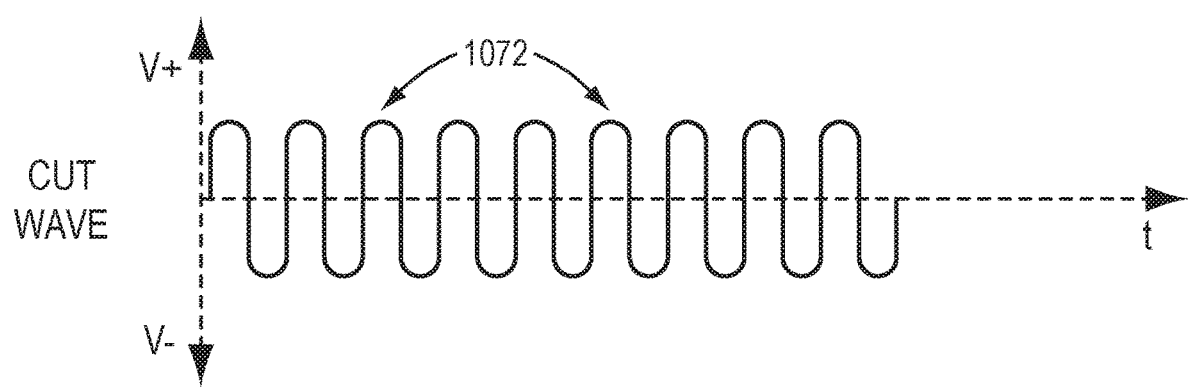

FIGS. 10A-10B depict exemplary coagulation and cut waveforms for enabling sealing and cutting operations, respectively. Each waveform represents a generator mode output from a flux generator such as an ESU to which the electrosurgical instrument is electrically connected, which results in the applied voltage over time across the electrodes of gripping end effector jaws. With reference to FIG. 10A, an exemplary coagulation waveform used for sealing operations is depicted. The waveform uses duty cycling, shown as by providing energy at portions 1068 of the waveform, and no energy at other portions 1070. This in turn results in heating, ceasing heating (cooling), and heating, which can provide ample time for the heat to generally dissipate, allowing proteins to cross link and shrink without excessively heating the tissue. Such energy application also allows the heatsink portions described in FIG. 10A to absorb the heat from a portion of tissue intended to be cut, which can preserve moisture in the tissue to facilitate the cutting operation. In contrast, the exemplary cutting waveform depicted in FIG. 10B generally provides a constant alternating current source of energy 1072. The constant application of energy, even at low voltages, heats up the tissue quickly and induces lysis/vaporization desirable for a cutting operation.

Various exemplary embodiments of the present disclosure include configuring geometries of a gripping end effector to achieve desirable gripping properties. In accordance with various exemplary embodiments, the upper and lower jaws can be configured to deliver varying pressure along a lateral length of an object being gripped by the jaws. For example, the geometry of one or more working surfaces of the gripping end effector may be adjusted such that while gripping, greater pressure is applied to the middle region, i.e. cutting region of the tissue versus other regions of the tissue. The greater pressure localized at the cutting region ensures a smoother cut, leaving behind fewer strands or "wisps" of tissue left uncut.

Figure 11:
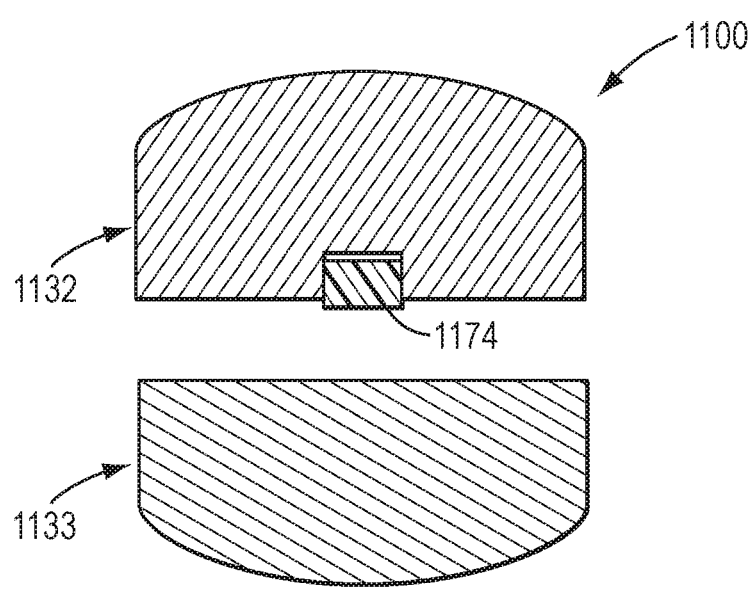
FIG. 11 is a cross-section view of an exemplary embodiment of a gripping end effector with a protrusion for applying pressure to material grasped with the gripping end effector.
Figure 12A:
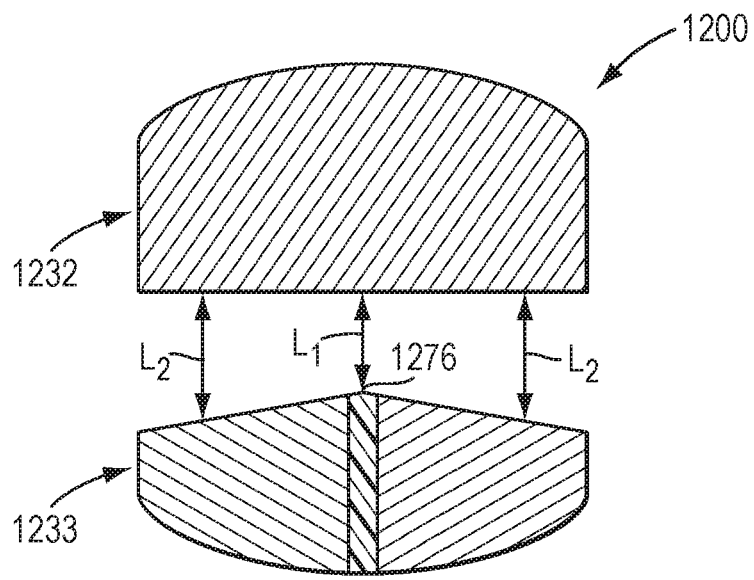
FIGS. 12A-12B show cross-section views of an exemplary embodiment of a gripping end effector with a convex apex for applying pressure to material grasped with the gripping end effector.
Figure 12B:
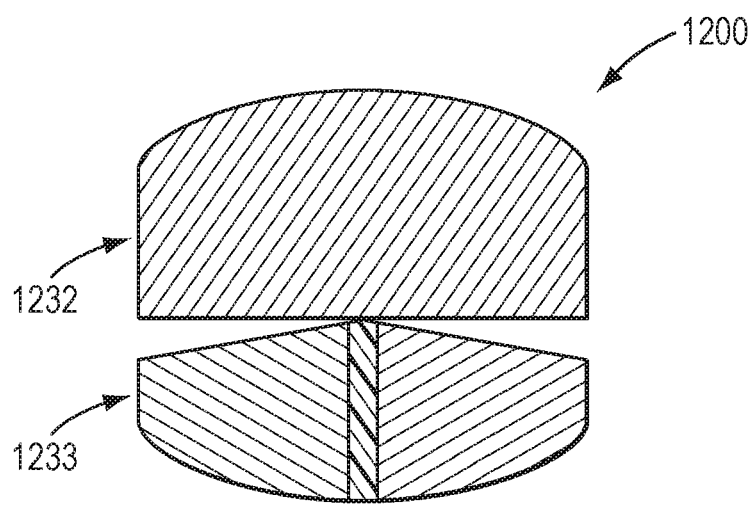

FIGS. 11 and 12 depict two different exemplary gripping end effectors for applying pressure to a region of tissue intended to be cut. In FIG. 11, upper jaw 1132 includes a protrusion 1174 that contacts a tissue such that, when gripped, greater pressure is applied to the middle of the tissue than to other regions of the tissue. Accordingly, when the cutting operation is performed, the greater pressure caused by protrusion 1174 cleanly separates the two pieces of tissue on either side of the cutting region. The protrusion 1174 may comprise any material such as plastic, etc. The protrusion 1174 may be a softer or elastic material that allows an object, such as tissue, to be gripped between jaws 1132 and 1133 without risk of damaging the tissue.

With reference to FIG. 12, the geometry of the lower jaw 1233 is configured with a convex apex 1276 on an upper surface of lower jaw 1233. In other words, an upper surface of each lower jaw portion 1234, 1238 is laterally tapered from the apex such that a distance $L_1$ between apex 1276 and the lower surface of upper jaw 1232 is smaller than a distance $L_2$ between each lateral edge of lower jaw 1233 and the lower surface of upper jaw 1232. Consequently, when an object such as tissue is compressed between the jaws, it is forced apart at apex 1276 such that a cut region is under tension from the force, enabling a cleaner separation when the cutting operation is performed.

Further modifications and alternative embodiments will be apparent to those of ordinary skill in the art in view of the disclosure herein. Other configurations of electrode placement, thermal and electrically conductive properties, sharp or rounded edges, materials, shapes, relative dimensions etc. can be used and modified to achieve various desired effects. For instance, wiring and positioning of the electrodes can be adjusted to target different energy flows for different types of end effectors. Material densities and thicknesses of an end effector can be varied depending on target structures that the end effector is applied to, such as different types of tissue that may react differently for a given thermal profile. Angles and geometries of the working surfaces can be varied to enable gripping of tissue types having different physical characteristics.

Further, the systems and the methods may include additional components or steps that were omitted from the diagrams and description for clarity of operation. Accordingly, this description is to be construed as illustrative only and is for the purpose of teaching those skilled in the art the general manner of carrying out the present teachings. It is to be understood that the various embodiments shown and described herein are to be taken as exemplary. Elements and materials, and arrangements of those elements and materials, may be substituted for those illustrated and described herein, parts and processes may be reversed, and certain features of the present teachings may be utilized independently, all as would be apparent to one skilled in the art after having the benefit of the description herein. Changes may be made in the elements described herein without departing from the spirit and scope of the present teachings and following claims. The nature of information depicted in the figures and described herein is exemplary. Those persons having skilled in the art would appreciate modifications to the displays can be made, such as, for example, depending on the number and type of controls desired, the number and/or type of instruments to be used, and/or the functions of the instruments used and the type of fluxes supplied by flux supply units. The various instrument setups depicted in the drawings and described herein are exemplary in nature and the present disclosure contemplates other instrument setups.

This description's terminology is not intended to limit the invention. For example, spatially relative terms—such as "beneath", "below", "lower", "above", "upper", "proximal", "distal", and the like—may be used to describe one element's or feature's relationship to another element or feature as illustrated in the figures. These spatially relative terms are intended to encompass different positions (i.e., locations) and orientations (i.e., rotational placements) of a device in use or operation in addition to the position and orientation shown in the figures. For example, if a device in the figures is turned over, elements described as "below" or "beneath" other elements or features would then be "above" or "over" the other elements or features. Thus, the exemplary term "below" can encompass both positions and orientations of above and below. A device may be otherwise oriented (rotated 90 degrees or at other orientations) and the spatially relative descriptors used herein interpreted accordingly.

It is to be understood that the particular examples and embodiments set forth herein are nonlimiting, and modifications to structure, dimensions, materials, and methodologies may be made without departing from the scope of the present teachings. Other embodiments in accordance with the present disclosure will be apparent to those skilled in the art from consideration of the specification and practice of the invention disclosed herein. It is intended that the specification and examples be considered as exemplary only, with a scope of the following claims being entitled to their broadest interpretation, including equivalents.

What is claimed is:

1. An electrosurgical instrument, comprising:
   a pair of jaw members configured to move between an open position and a closed position, wherein in the closed position the pair of jaw members is configured to exert a gripping force on material placed between opposing first and second working surfaces of the pair of jaw members, the first and second working surfaces each having a longitudinal dimension and a lateral dimension;
   wherein a first jaw member of the pair of jaw members comprises a first conductive shell surrounding a first insulative core in a cross-section of the first jaw member transverse to the longitudinal dimension, the first conductive shell forming a first electrode defining the first working surface of the pair of jaw members;
   wherein a second jaw member of the pair of jaw members comprises a second electrode and a third electrode disposed at opposite lateral side portions of the second jaw member, and a dielectric material separating the second electrode and the third electrode, wherein the second electrode, the third electrode, and the dielectric material define the second working surface of the pair of jaw members; and
   wherein a thermal conductivity of the first electrode is greater at a middle of the first working surface than at lateral portions of the first working surface such that a thermal profile of the first working surface varies along a lateral dimension of the first working surface.

2. The electrosurgical instrument of claim 1, wherein the dielectric material extends along the longitudinal dimension of the second working surface.

3. The electrosurgical instrument of claim 1, wherein the dielectric material is one of ceramic, plastic, and combinations of ceramic and plastic.

4. The electrosurgical instrument of claim 1, wherein the second jaw member comprises a second conductive shell and a third conductive shell made of an electrically conductive material and forming the second and third electrodes, respectively.

5. The electrosurgical instrument of claim 4, wherein the first conductive shell is made of the electrically conductive material and the electrically conductive material is steel.

6. The electrosurgical instrument of claim 4, wherein the second conductive shell surrounds a second insulative core in a cross-section of the second jaw member transverse to the longitudinal dimension and the third conductive shell surrounds a third insulative core in a cross-section of the second jaw member transverse to the longitudinal dimension.

7. The electrosurgical instrument of claim 6, wherein the electrically insulating material is one of ceramic, plastic, and combinations of ceramic and plastic.

8. The electrosurgical instrument of claim 6, wherein the thermal conductivity of the first electrode varies based on variations in a thickness of the first conductive shell of the first jaw member.

9. The electrosurgical instrument of claim 8, wherein each of the first, second, and third conductive shells are thinner at outer lateral regions of the jaw members and thicker at a middle region of the jaw members disposed between the outer lateral regions.

10. The electrosurgical instrument of claim 4, wherein at least one of the second and third electrodes comprises a first sharp corner disposed adjacent to the dielectric material on the second working surface of the second jaw member.

11. The electrosurgical instrument of claim 10, wherein the first sharp corner is configured to concentrate electrical energy applied to the one of the second and third electrodes.

12. The electrosurgical instrument of claim 10, wherein the first electrode comprises a second sharp corner on the first working surface of the first jaw member, the second sharp corner disposed on a portion of the first working surface of the first jaw member corresponds to a position of the first sharp corner on the second working surface of the second jaw member.

13. The electrosurgical instrument of claim 1, wherein the first working surface of the first jaw member comprises a protrusion disposed at a middle portion of the first working surface of the first jaw member.

14. The electrosurgical instrument of claim 13, wherein the protrusion is made of a material chosen from at least one of plastic and an elastic material.

15. The electrosurgical instrument of claim 1, wherein the second working surface of the second jaw member comprises a convex apex at a middle portion of the second working surface of the second jaw member.

16. The electrosurgical instrument of claim 15, wherein the second working surface of the second jaw member is laterally angled from the convex apex, such that a distance between the convex apex and the first working surface of the first jaw member is smaller than a distance between lateral edges of the second jaw member and opposing lateral surface of the first jaw member.

17. The electrosurgical instrument of claim 1, further comprising an interface configured to couple the electrosurgical instrument to a teleoperated surgical system.

18. The electrosurgical instrument of claim 17, wherein the interface further comprises individual connectors for each of the first, second, and third electrodes, the individual connectors configured to conduct electrical energy.

19. A surgical system, comprising:
   an electrosurgical instrument; and
   an electrosurgical energy supply source electrically coupled to supply electrical energy to the electrosurgical instrument;
   wherein the electrosurgical instrument comprises a first jaw member comprising a first electrode, and a second jaw member comprising a second electrode and a third electrode,
   wherein the first and second jaw members are configured to grasp a material between opposing first and second working surfaces of each of the first and second jaw members, the first and second working surfaces each having a longitudinal dimension and a lateral dimension,
   wherein a thermal conductivity of a portion of one or more of the first, second, and third electrodes is greater than at other portions of the one or more of the first, second, and third electrodes, respectively, such that a thermal profile of one or both of the first working surface and the second working surface varies along a lateral dimension of one or both of the first and second working surfaces, and
   the electrosurgical energy supply source is configured to selectively alter a polarity of each of the first, second, and third electrodes, to change a state of the instrument between a first state and a second state such that:
- in the first state, the first electrode has a first polarity chosen from a positive or a negative polarity, and the second and third electrodes both have a second polarity chosen from a positive or a negative polarity and that is opposite the first polarity; and
- in the second state, the first electrode has a neutral polarity, the second electrode has a positive polarity, and the third electrode has the negative polarity.

20. The surgical system of claim 19, wherein the electrosurgical energy supply source is configured to alter the polarity of each of the first, second, and third electrodes independently.

21. The surgical system of claim 19, wherein the first working surface of the first jaw member comprises a protrusion disposed at a middle portion of the first working surface of the first jaw member.

22. The surgical system of claim 21, wherein the protrusion is made of a material chosen from at least one of a plastic an elastic material.

23. The surgical system of claim 19, wherein the second working surface of the second jaw member comprises a convex apex at a middle portion of the second working surface of the second jaw member.

24. The surgical system of claim 23, wherein the second working surface of the second jaw member is laterally angled from the convex apex, such that a distance between the convex apex and the first working surface of the first jaw member is smaller than a distance between lateral edges of the second jaw member and opposing lateral surfaces of the first jaw member.

25. The electrosurgical instrument of claim 1, wherein:
- in a cross-section taken transverse to the longitudinal dimension of the second jaw member, the second jaw member comprises a second conductive shell surrounding a second insulative core and a third conductive shell surrounding a third insulative core, the second conductive shell forming the second electrode and the third conductive shell forming the third electrode.

26. The electrosurgical instrument of claim 25, wherein:
- the first conductive shell comprises two thin portions and a thick portion collectively forming the first working surface of the first jaw member and extending continuously across the lateral dimension of the first working surface, the thick portion being thicker than the thin portions; and
- the thick portion includes a longitudinal center of the first working surface of the first jaw member between the thin portions.

27. The electrosurgical instrument of claim 26, wherein:
- the second and third conductive shells each comprise respective thin portions and respective thick portions thicker than the thin portions; and
- the respective thick portions of the second and third conductive shells are disposed opposite from the thick portion of the first conductive shell.

28. The electrosurgical instrument of claim 26, wherein:
- a dielectric material separates the second and third conductive shells from one another; and
- the dielectric material is disposed at a middle portion of the second jaw member opposite from the thick portion of the first conductive shell.

29. The electrosurgical instrument of claim 1, wherein the second working surface of the second jaw member consists of the dielectric material and the second and third electrodes.

30. The electrosurgical instrument of claim 1, wherein:
- the first conductive shell comprises two thin portions and a thick portion collectively forming the first working surface of the first jaw member and extending continuously across the lateral dimension of the first working surface, the thick portion being thicker than the thin portions; and
- the thick portion includes a longitudinal center of the first working surface of the first jaw member between the thin portions.

* * * * *